(12) United States Patent
Digiacomantonio et al.

(10) Patent No.: US 9,456,932 B2
(45) Date of Patent: Oct. 4, 2016

(54) ABSORBENT ARTICLE HAVING LATERAL ZONES

(71) Applicant: The Procter & Gamble Company, Cincinnati, OH (US)

(72) Inventors: Marco Digiacomantonio, Pescara (IT); Cornelia Ecker, Schwalbach (DE); Ivano Gagliardi, Pescara (IT); Vincenzo Partenza, Pescara (IT); Paolo A. Veglio, Pescara (IT)

(73) Assignee: The Procter & Gamble Company, Cincinnati, OH (US)

( * ) Notice: Subject to any disclaimer, the term of this patent is extended or adjusted under 35 U.S.C. 154(b) by 264 days.

(21) Appl. No.: 13/895,548

(22) Filed: May 16, 2013

(65) Prior Publication Data

US 2013/0245587 A1 Sep. 19, 2013

Related U.S. Application Data

(63) Continuation of application No. 11/732,579, filed on Apr. 4, 2007, now Pat. No. 8,461,411.

(51) Int. Cl.

| A61F 13/15 | (2006.01) |
|---|---|
| A61F 13/51 | (2006.01) |
| A61F 13/475 | (2006.01) |
| A61F 13/537 | (2006.01) |
| A61F 13/472 | (2006.01) |
| A61F 13/513 | (2006.01) |
| A61F 13/84 | (2006.01) |

(52) U.S. Cl.
CPC ........... *A61F 13/475* (2013.01); *A61F 13/472* (2013.01); *A61F 13/4755* (2013.01); *A61F 13/4757* (2013.01); *A61F 13/51394* (2013.01); *A61F 13/53747* (2013.01); *A61F 2013/15536* (2013.01); *A61F 2013/51377* (2013.01); *A61F 2013/8497* (2013.01)

(58) Field of Classification Search
CPC ............... A61F 13/51394; A61F 2013/15243; A61F 2013/51377; A61F 2013/8497
See application file for complete search history.

(56) References Cited

U.S. PATENT DOCUMENTS

| 4,623,340 | A | * | 11/1986 | Luceri ...................... 604/385.05 |
|---|---|---|---|---|
| H1376 | H | * | 11/1994 | Osborn et al. ................. 604/361 |
| 5,431,643 | A | | 7/1995 | Ouellette et al. |
| 5,533,991 | A | | 7/1996 | Kirby et al. |
| 6,365,795 | B1 | | 4/2002 | Suekane et al. |
| 6,586,653 | B2 | | 7/2003 | Graeme, III et al. |
| 6,932,798 | B2 | * | 8/2005 | Kudo et al. ............. 604/385.01 |
| 6,984,770 | B2 | | 1/2006 | Graeme, III et al. |
| 2003/0078553 | A1 | * | 4/2003 | Wada et al. ................... 604/361 |

(Continued)

FOREIGN PATENT DOCUMENTS

| EP | 1108406 | 7/2001 |
|---|---|---|
| EP | 0 523 683 B2 | 10/2002 |

(Continued)

*Primary Examiner* — Lynne Anderson
(74) *Attorney, Agent, or Firm* — George H. leal; Andrew J. Hagerty

(57) ABSTRACT

An absorbent article for collecting bodily fluid having a topsheet, a backsheet and an absorbent structure. The article may include a central fluid acquisition zone, a first lateral zone situated on one side of the central zone and a second lateral zone situated on the opposite side of the central zone, wherein the first and second lateral zones are formed by a nonwoven material.

40 Claims, 7 Drawing Sheets

(56) References Cited

U.S. PATENT DOCUMENTS

| | | |
|---|---|---|
| 2003/0109839 A1 | 6/2003 | Costea et al. |
| 2003/0114809 A1 | 6/2003 | Gagliardi et al. |
| 2003/0114811 A1* | 6/2003 | Christon et al. ............... 604/362 |
| 2003/0204178 A1 | 10/2003 | Febo et al. |
| 2004/0015145 A1* | 1/2004 | Miura et al. .................. 604/367 |
| 2004/0122398 A1* | 6/2004 | Schnabel et al. ........ 604/385.01 |
| 2004/0133181 A1* | 7/2004 | Ishiguro et al. ......... 604/385.28 |
| 2005/0096618 A1* | 5/2005 | Magee et al. ............ 604/385.01 |
| 2005/0148961 A1* | 7/2005 | Sosalla et al. ................ 604/361 |
| 2006/0129114 A1* | 6/2006 | Mason et al. ................. 604/361 |
| 2006/0142710 A1* | 6/2006 | Kigata et al. ................. 604/361 |
| 2007/0087169 A1* | 4/2007 | McFall ......................... 428/172 |
| 2007/0093770 A1* | 4/2007 | Ecker et al. ............. 604/385.01 |

FOREIGN PATENT DOCUMENTS

| | | |
|---|---|---|
| JP | 2004230127 | 8/2004 |
| WO | WO 93-09744 A1 | 5/1993 |
| WO | WO9741818 | 11/1997 |
| WO | WO 00-74620 A1 | 12/2000 |
| WO | WO 02-07662 A1 | 1/2002 |
| WO | WO 02-076339 A2 | 10/2002 |
| WO | WO 2004-060242 A1 | 7/2004 |

* cited by examiner

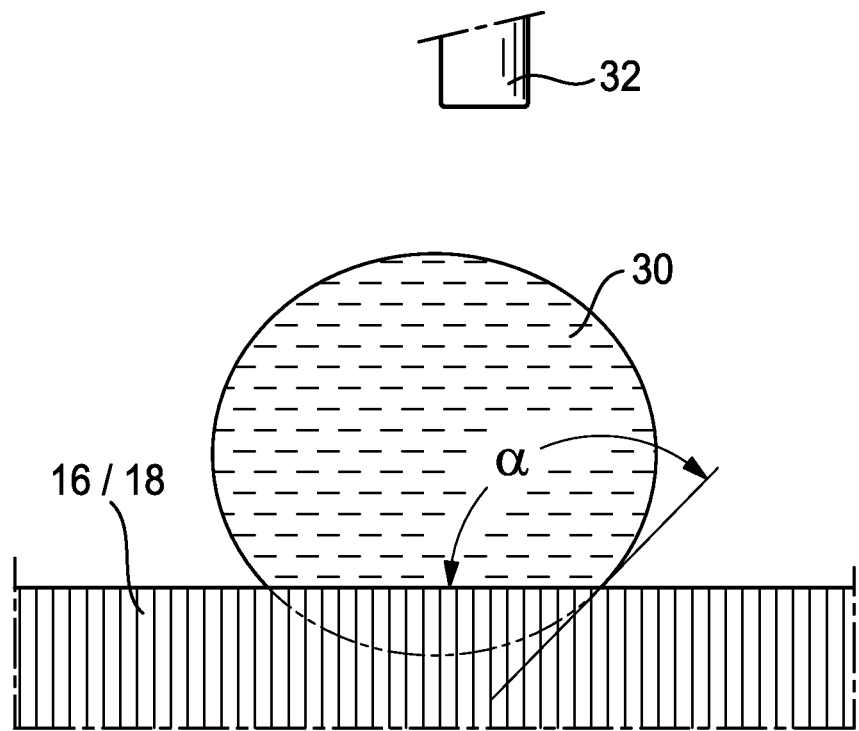

ABSORBENT ARTICLE HAVING LATERAL ZONES

FIELD OF THE INVENTION

The invention relates to absorbent hygiene articles for collecting bodily fluids, in particular feminine hygiene articles of the type commonly referred to as sanitary napkins. The articles claimed comprise on their body-facing surface i) a central fluid acquisition zone which may be substantially white and ii) two nonwoven lateral zones.

BACKGROUND OF THE INVENTION

Feminine hygiene articles are used by women during their menstrual periods to receive and contain blood discharges from the vagina. In addition to collecting menses, these absorbent sanitary articles may also be used to protect the wearer's undergarment from other bodily fluids such as urine in the case of light incontinence of the user. These articles are generally flat and comprise a body-facing surface, an opposite garment-facing surface and absorbent structure, normally referred to as an absorbent core, placed in-between. The body-facing surface of the article is the first exposed to the flow of the bodily fluid, which is then absorbed and directed to the absorbent structure. The garment-facing side of the article normally comprises at least one fluid impermeable layer to prevent the fluid from leaking from the absorbent structure to the garment.

In the past, it was common for the body-facing surface of feminine hygiene articles to be entirely made of a liquid pervious topsheet that let or lead the fluid to the inner absorbent structure. More recently, so called "hybrid" topsheets have been proposed wherein a central acquisition layer is flanked by lateral outer layers of a different material. For example WO 93/09744 (Procter & Gamble) discloses an absorbent article with a nonwoven outer layer having an opening positioned in the central zone and apertured thermoplastic film layer positioned beneath the outer layer. This topsheet is said to be improving the feel and comfort of the user. U.S. Pat. No. 5,533,991 and EP 523,683 A1 (both to Kimberly-Clark) disclose absorbent articles which includes two different materials on the body-side cover.

However the components of these hybrid topsheets have only been proposed in a single shade, usually white. An exception to the traditional white products is found in WO 02/07662 (Procter & Gamble), where dark colored absorbent articles such as sanitary napkins or pantiliners are proposed. However the surface of these articles is entirely black and does not have the traditional white appearance that the consumer expects to find for feminine hygiene articles of this category. Hybrid topsheets having lateral zones of a shade which differs from the central zone have not been disclosed. In particular, it has not been proposed in the prior art to use colored (by colored we mean non-white) pigments in selected portions of the topsheet only, rather than the whole surface of the topsheet as in WO 02/07662.

Among the numerous attempts to improve the properties of sanitary articles, it has also been proposed to apply certain compositions on selected parts of the articles. For example WO 02/076339 (Paragon Trade Brands) discloses absorbent articles having hydrophobic leak protection zone on the body-facing surface of the article. The hydrophobic substance is preferably cocoa butter. WO 2004/060242A1 discloses feminine care products having a band of spaced apart deposits of a barrier substance material on the top cover. The bands are said to act as a fluid barrier against lateral flow of bodily fluids.

Although it has been proposed in the past to apply colored composition to lateral zones of the topsheet of absorbent articles, it remains technically difficult to apply or print a colored composition on absorbent of articles in a precise way, in particular if the color is applied in a pattern other than a straight line. This is at least because it may be difficult and costly to continuously monitor the high-speed production lines to detect and correct the inevitable displacement in the machine direction or in the machine transversal direction that may occur during printing, resulting in accidental misplacement of the composition when it is applied.

In another aspect of the ongoing development of absorbent articles, it has been proposed to use gradient cores instead of the traditional laminate cores. Gradient absorbing core materials (herein "gradient core") are designed to quickly absorb fluid from the top of the core's surface to its bottom and then distribute in the horizontal plane direction. This is usually achieved by a unitary multistratum construction which is anisotropic in the vertical direction for fast fluid acquisition. The material stratum density and the average pore size decrease from top to the bottom of the core to drive the bodily fluid to the bottom of the core. A typical example of gradient core can be found in WO 0074620A1 (to BKI).

Although the intensity of the stain around the fluid impact zone (the aureole) at the surface of the core is lower in the so-called gradient cores than with traditional laminates cores or other absorbent structures, the stain sizes may by comparatively larger because the fluid is not uniformly propagated in the thickness of the core but concentrate in the bottom of the gradient core. It would be desirable to mask this increase in stain size when using gradient core.

Continual improvements in technology have led to absorbent products having excellent fluid absorption and retention properties. However some of the common problems still associated with these articles include leakage of the bodily fluids through the lateral edges of the articles and re-wetting of the body-facing surface. Re-wetting happens when bodily fluid already absorbed in the absorbent structure resurface, for example due to the pressure exerted on the core by the user's movement.

Furthermore, although the prior art has focused on leakage prevention and improved feel, there is still a need for absorbent articles with a better visual appearance. Before use, it would be beneficial to improve the appearance of absorbent articles in a way which is economical and practical. After use, it would be beneficial to mask or reduce the size of the stains on the body-facing surface of the articles.

SUMMARY OF THE INVENTION

The inventors have found that some of the shortcomings of the prior art may be addressed by the articles presently claimed. The invention is directed to absorbent hygiene articles, such as, but not limited to, feminine pads or liners. The articles comprise a body-facing surface, a garment facing-surface and an absorbent structure situated between the body-facing surface and the garment-facing surface. The body-facing surface of such articles may be conceptually (i.e. not physically) divided in its length in two halves by a longitudinal centerline L and its width by a transversal centerline T.

In a first aspect of the present invention, the body-facing surface of the article comprises:

i) a central fluid acquisition zone, which may be substantially white, ii) a first visually discernible lateral zone situated on one side of the central fluid acquisition zone and, iii) a second visually discernible lateral zone situated on an opposite side of the central fluid acquisition zone, and wherein the first and second lateral zones are made of a nonwoven material comprising a colored pigment. In one embodiment, the first and second lateral zones are at least partially situated above the absorbent structure. Also the nonwoven material(s) forming the lateral zones may be sufficiently opaque to be able to mask to a certain extent underlying stains.

In a second aspect of the invention, the article's absorbent structure comprises or consists of a gradient core and the body-facing surface of the article comprises:

i) a central fluid acquisition zone, which may be substantially white, ii) a first hydrophobic lateral zone situated on one side of the central fluid acquisition zone and, iii) a second hydrophobic lateral zone situated on the opposite side of the central fluid acquisition zone, wherein the first and second hydrophobic lateral zones are made of a hydrophobic nonwoven material. In one embodiment, the hydrophobic nonwoven material contains pigments, preferably colored pigments, and has some opacity to mask the underlying stains to a certain extent.

In both aspects, the central fluid acquisition zone may encompass the longitudinal centerline or the transversal centerline.

Of course, an embodiment of the present invention may advantageously combine the features of the first aspect and second aspect of the present invention.

BRIEF DESCRIPTION OF THE DRAWINGS

While the specification concludes with claims which particularly point out and distinctly claim the invention, it is believed the present invention will be better understood from the following description of preferred embodiments taken in conjunction with the accompanying drawings, in which like reference numerals identify identical elements and in which:

FIG. 8 shows how the hydrophobicity of a sample can be measured by determining the contact angle of a drop of water.

DETAILED DESCRIPTION OF THE INVENTION

Definitions

Unless explicitly stated otherwise, the term "comprising" is to be construed as open ended, meaning that other features, steps or ingredients can be added as long as they are suitable to be used in an absorbent hygiene article.

As used herein, the term "absorbent hygiene articles" refers to the type of absorbent articles worn externally to collect bodily fluid such as menses, urine, feces or blood and include infant diapers, incontinent briefs, incontinent pads, training pants, diaper inserts, panti-liners, catamenial pads, sanitary napkins, menstrual pads, tampons, bandages, surgical dressings and the like. The term "disposable" refers to the articles which are normally discarded after use, without being washed to be reused. The articles claimed are preferably disposable.

The term "feminine hygiene articles" refers to the type of absorbent hygiene articles externally worn by women, usually for menstrual and/or light incontinence control. These articles are commonly referred to as pads, pantiliners, liners, sanitary napkins or sanitary towels. These articles have generally flat surfaces and are typically held in place adjacent the user's crotch (i.e. the pubic region) by the user's undergarment on which they are affixed via adhesive or other joining means. In what follows, the invention is mainly exemplified as a disposable feminine hygiene article but is also applicable to other type of disposable hygiene articles such as diapers or wound bandages.

The term "body-facing surface" refers to the side of the absorbent article facing the body of the user when in use. The "garment-facing surface" is the opposite surface of the article.

Figure 3:
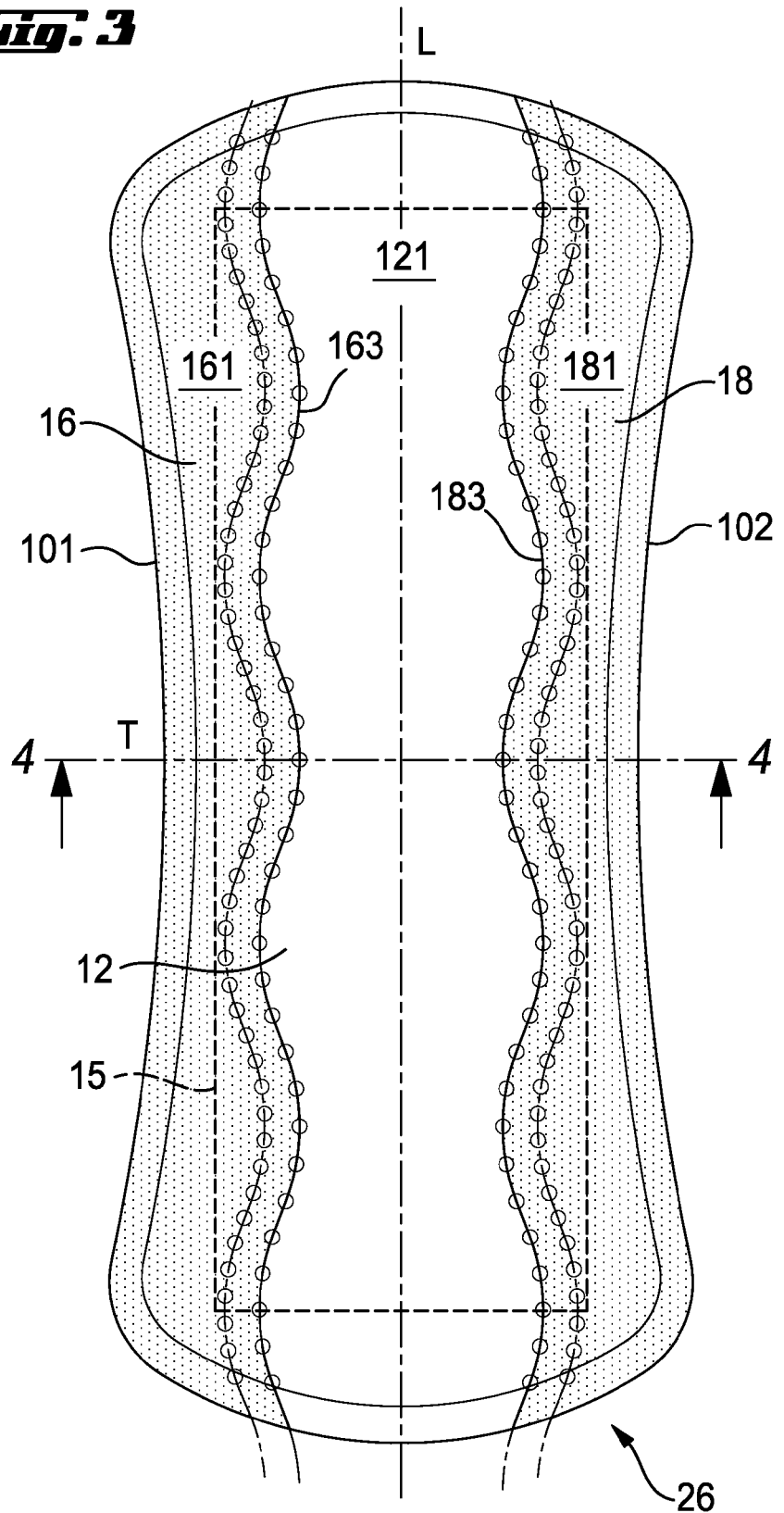
FIG. 3 is a top view of the body-facing surface of the embodiment of FIG. 1.
Figure 4:
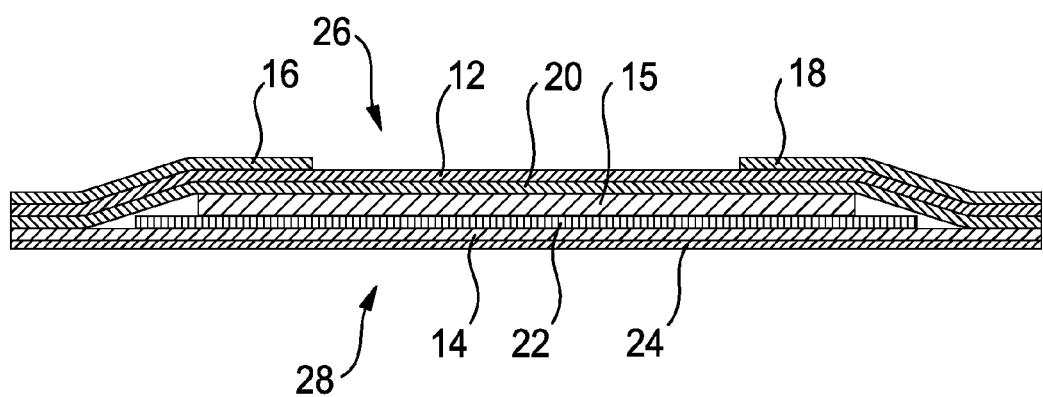
FIG. 4 is cross section view of the article of FIG. 1.

The term "longitudinal centerline" refers to the imaginary line centered between the longitudinal side edges (left and right as represented in FIG. 3) of the article and which is generally aligned with the vertical plane which bisects a standing wearer into left and right body halves. The longitudinal centerline is represented by the line L on the drawings. The longitudinal centerline conceptually divides the article in two halves. By conceptually we mean that the longitudinal centerline is normally not physically present or visible in the article.

The term "transversal centerline" refers to the imaginary line which is perpendicular to the longitudinal centerline in the plane of the body-facing surface and intersects it in the middle of the length of the article as measured on the longitudinal centerline. The transversal centerline conceptually divides the article in two halves. By conceptually we mean that the transversal centerline is normally not physically present or visible in the article.

Absorbent Article 10

Figure 1:
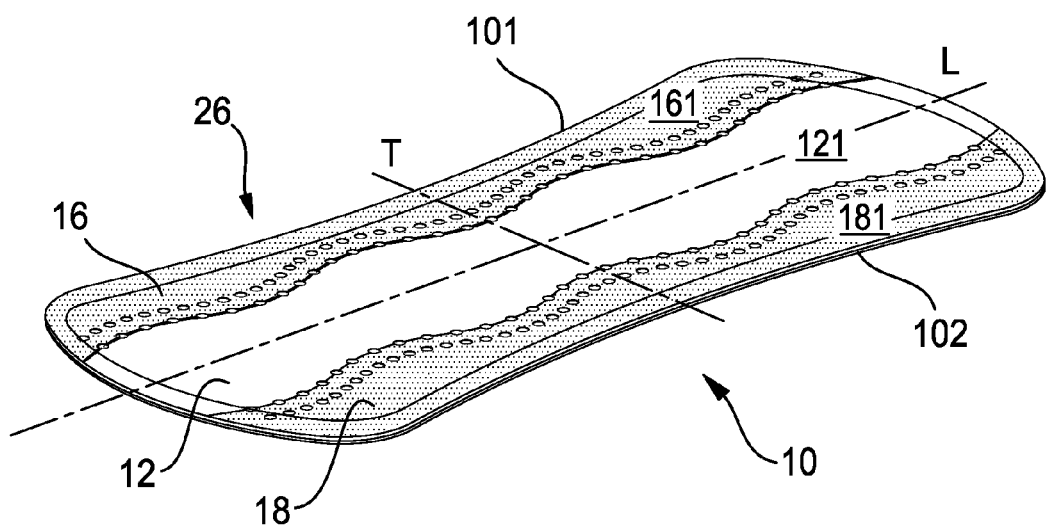
FIG. 1 is a perspective view of an exemplary feminine hygiene article according to the invention.

FIG. 1 shows a perspective view of the body-facing surface of an exemplary absorbent article 10 according to the invention, herein represented as a feminine hygiene article in a typical liner configuration. The articles of the invention normally have a generally flat body-facing surface but may be curved to conform to the user's body and are generally flexible to adapt to the user's anatomy. However the feminine hygiene articles of the invention are not limited to a specific design construction.

The dimensions of the articles of the invention are adapted for the use intended as in known in the art. For example, pantiliners ("liners") are generally smaller and compacter than pads. The thickness of the absorbent articles usually ranges from about 2 mm to about 50 mm. Thin sanitary napkin articles can have a thickness of less than about 6 mm, or even less than about 4 mm.

The length of the article along the longitudinal centerline L of the article may typically be between 10 cm and 25 cm, more typically between 12 cm and 21 cm. The width of the article along the transversal centerline may typically be between 3 and 10 cm, more typically between 4 and 7 cm. Typically the total surface area of the body facing side of a liner is between 50 and 150 cm$^2$, a pad between 60 and 200 cm$^2$ and diapers even larger. A typical surface area for a normal liner may be around 80 cm$^2$. All these dimensions are merely indicative and not limitative, because the normal dimensions of these and other types of absorbent sanitary articles may differ according to the intended use, as is known in the art.

Figure 2:
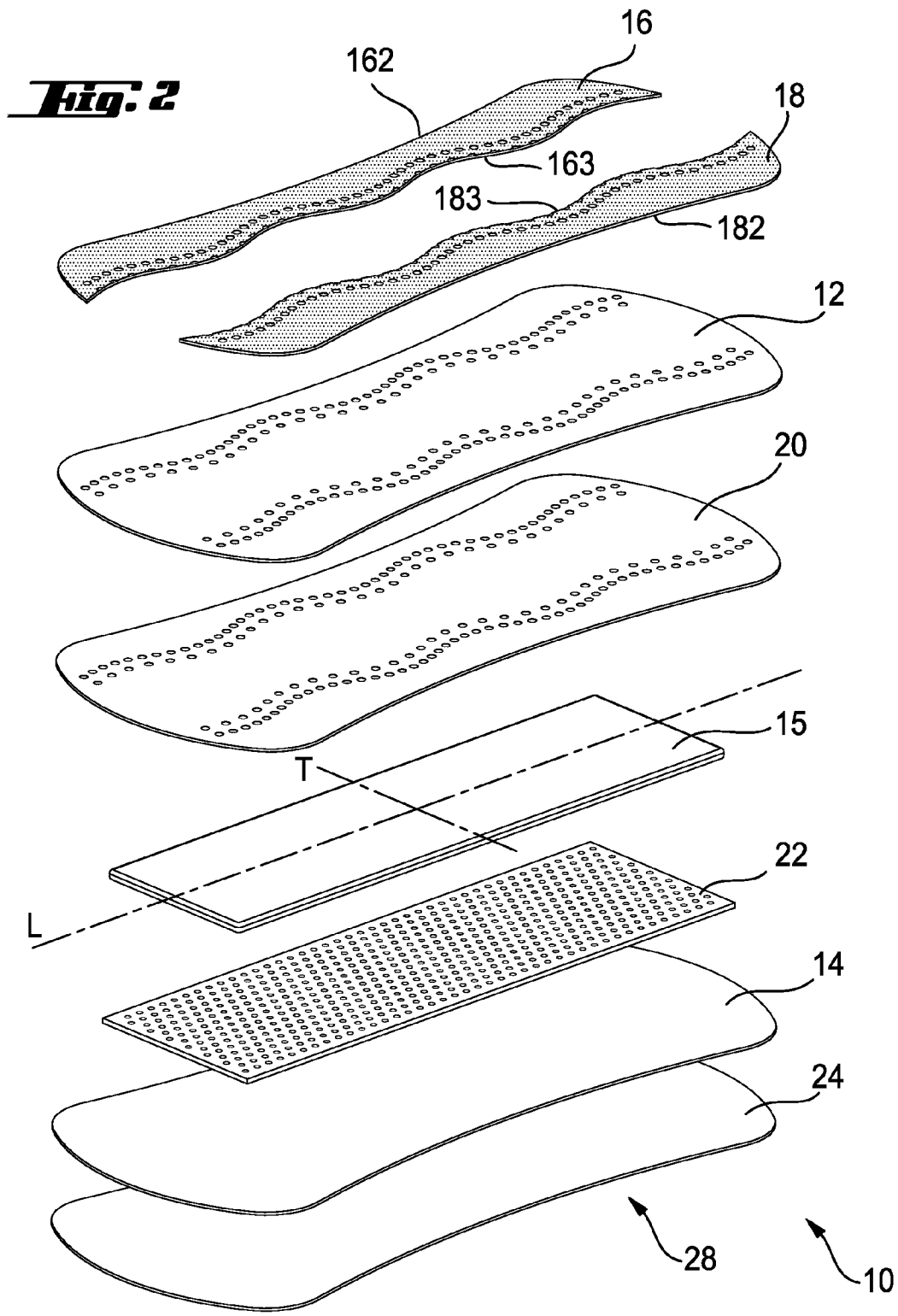
FIG. 2 is an exploded view of the article of FIG. 1.

FIG. 2 shows the different components or layers of the exemplary embodiment of FIG. 1. The articles of the invention comprise a topsheet 12, a backsheet 14, and an absorbent structure 15 situated between the topsheet 12 and backsheet 14. As represented, the topsheet may form the central fluid acquisition zone of the body-facing surface of the article, whilst the backsheet forms the garment-facing surface. Two strips of a nonwoven material 16, 18 are disposed on each side of the longitudinal centerline and form the first lateral zone 161 and second lateral zone 181 of the invention. Further additional elements to improve the performance of the articles may also be used and are represented in the Figures, such as a secondary topsheet 20, and/or a secondary backsheet 22. The article may also comprise a release paper 24.

Absorbent hygiene articles are usually substantially symmetrical in relation to the longitudinal centerline, such that the longitudinal centerline divides the article in two substantially symmetrical halves (notwithstanding possible decorations such as embossments or printed patterns). However although this is preferred, it is not necessary so, for example it has been proposed to use feminine articles with wings which are offset in relation to each other.

Body-Facing Surface

The articles of the invention have a generally flat body-facing surface 26, which may normally enter at least partially in contact with the user's body when it is worn. The body-facing surface of the article comprises a central fluid acquisition zone 121, which may be substantially white, and a first and second lateral zones 161, 181. The body-facing surface of the article is advantageously embossed. The embossment pattern 28 may be continuous or discontinuous and preferably bonds several layers of the articles. As shown in FIGS. 2-3, the embossment pattern 28 advantageously bonds the lateral topsheet strips 16, 18 to the topsheet 12 and the secondary topsheet strip 20 underneath. The embossment pattern preferably at least partially overlaps the lateral topsheet strips 16, 18.

Central Fluid Acquisition Zone

The articles of the invention have a central fluid acquisition zone 121, which may be substantially white. By substantially white, we mean that central fluid acquisition zone has the typical white appearance of the articles of the category considered, such as feminine hygiene articles or incontinence product. Consumers associate this white appearance with cleanliness and hygiene. By "substantially white" we do not mean that the whole surface of the central fluid acquisition zone need not be white, as it has become common to provide articles having central fluid acquisition zones comprising printed decorations, see for example EP 1,295,711 A1, as long as a substantial portion of the central fluid acquisition zone is white, typically at least 30% by surface, or at least 50%. The central fluid acquisition zone normally receives the major part of the bodily fluid before directing it within the absorbent structure and represents at least 25% of the surface of the body-facing surface. The surface of the central fluid acquisition zone represents typically between 30% and 70% of the total surface of the body-facing surface of the article.

Figure 5:
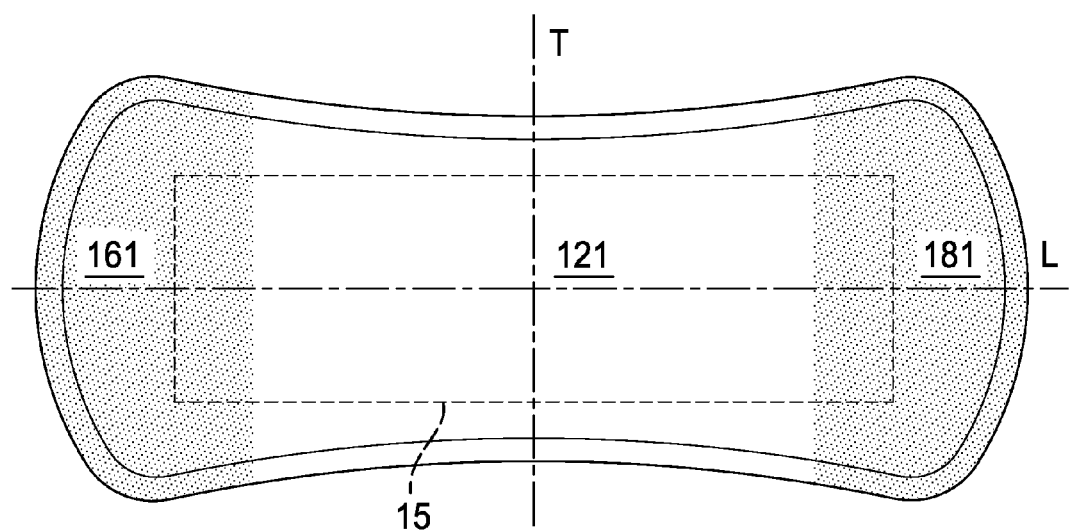
FIG. 5 is a top view of the body-facing surface of an alternative embodiment of FIG. 1.
Figure 6:
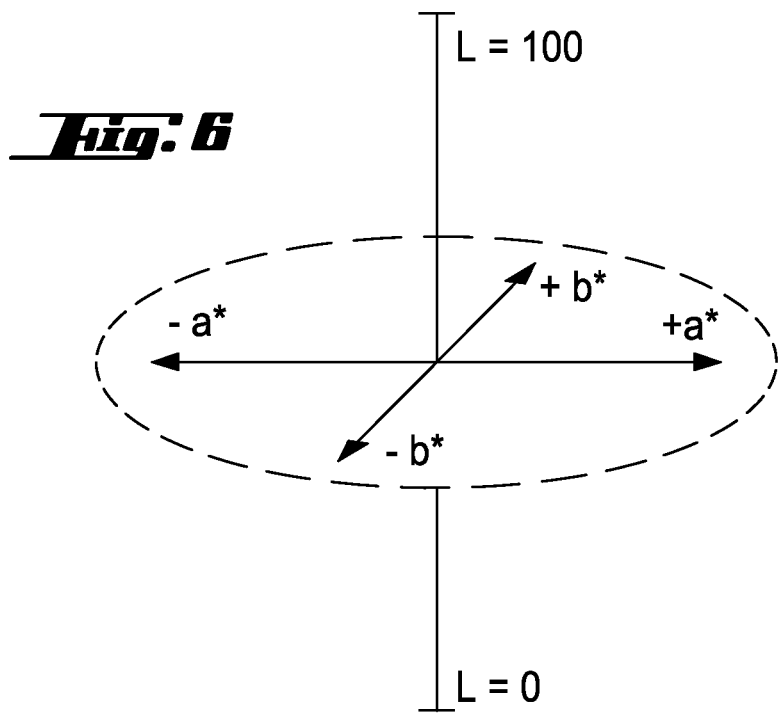
FIG. 6 shows the color "sphere" used for the representation of color in the CIELAB system.

The central fluid acquisition zone may encompass the longitudinal centerline L (as exemplarily shown in FIG. 3) or the transversal centerline T (as in FIG. 5), partially or in their totality. It may be preferred that at least 50% in length of at least one of these axis to be encompassed within the central fluid acquisition zone.

As shown on FIG. 3, the central fluid acquisition zone may be formed by the topsheet layer 12 of the article. Any conventional topsheet material may be used herein. The topsheet is a layer of the article that contacts the body of the wearer and primarily receives bodily discharges. The topsheet is liquid pervious and may be flexible and non-irritating to the skin. The term "liquid pervious" as used herein refers to components that allow liquids to pass therethrough without significantly retarding or obstructing the transmission of such liquids therethrough. As used herein the term "flexible" refers to materials which are compliant and readily conform to the shape of the body or respond by easily deforming in the presence of external forces. Components are considered absorbent if such components not only transmit such liquids, but also can retain a portion of the liquids deposited on such components.

Any conventional topsheet materials may be used within the invention. The topsheet should be sanitary, clean in appearance and preferably not noisy to provide discretion for the wearer. Suitable topsheets may be made from nonwoven materials or perforated polyolefinic films.

If desired, the topsheet may be sprayed with a surfactant to enhance liquid penetration to the core. The topsheet and in particular the central fluid acquisition zone may thus advantageously be hydrophilic. The surfactant is typically non-ionic and should be nonirritating to the skin. A surfactant density of about 0.01 milligrams per square centimeter of topsheet area is normally suitable. A suitable surfactant is sold by the Glyco Chemical, Inc. of Greenwich, Conn. as Pegosperse 200 ML.

The topsheet may have a plurality of apertures to permit liquids deposited thereon to pass through to the core. An apertured polyolefinic film topsheet having about 5 to about 50 percent open area, typically about 25 percent open area, and a thickness of about 0.01 to about 0.05 millimeters prior to aperturing and about 0.42 to about 0.51 millimeters after aperturing is usual.

A suitable apertured topsheet for use herein are nonwoven topsheet. Suitable nonwoven materials/layers include fibrous nonwoven materials/layers formed by a carding process or a spunbond process or meltblown process whereby molten polymeric material is extruded through a die, attenuated to lengthen the extruded polymer into fibers and decrease the diameter thereof and is subsequently deposited on a forming surface. Methods of forming such nonwoven materials/layers are known to those skilled in the art. Polymeric materials suitable for use in forming such fibrous nonwoven materials/layers include polyolefins such as polyethylene and polypropylene, polyesters, nylons, ethylene vinyl acetate, ethylene methacrylate, copolymers of the above materials, block copolymers such as A-B-A block copolymers of styrene and butadiene, and the like.

As discussed above, the central fluid acquisition zone may be substantially white. The "whiteness" of a substrate can be quantified by using the L*, a*, b* value on the CIELAB Color scale. In short, in this scale the L value defines the lightness and ranges from 0 to 100, with 0 being absolute black and 100 absolute white. A description of the CIELAB scale system is present in details in the Experimental section below. The central fluid acquisition zone may in one embodiment have an L* Hunter value of at least 90 or higher (for example at least 95, or even at least 97), with the absolute value of each a* and b* being preferably below 1, or even below 0.5 as measured directly on the central fluid acquisition zone of the article. If the central zone has colored decorations, these values are measured in non-decorated spaces of the central zone.

Lateral Zones

The articles of the invention comprise a first lateral zone 161 and a second lateral zone 181, each lateral zone being placed on opposite sides of the central fluid acquisition zone (for example the first zone on the "left" half of the article, the second zone on the "right" half of the article when viewed from above as represented on FIG. 3). The lateral zones 161, 181 are made of a nonwoven material which is different from the material forming the central fluid acquisition zone 121. The lateral zones are preferably at least partially situated above the absorbent structure 15. By "above", we mean in a higher vertical position which overlays the absorbent structure. There may be one or more intermediate layer in between the lateral zones and the absorbent structure and the lateral zones need not be directly contacting the absorbent structure. For example, as represented in the FIG. 1-2, the topsheet and secondary topsheet may be placed intermediate the lateral zones and the absorbent structure. In a preferred embodiment as represented in these Figures, the lateral zones extend to the periphery of the article, in particular the lateral side edges of the periphery of the article. Both lateral zones are advantageously made of the same material for aesthetic and economical reasons but different materials may be used.

The lateral zones may be made of any conventional nonwoven materials, such as carded thermal bonded, spun bonded, hydro entangled, melt blown, and using all range of suitable synthetic or natural fibers such as polypropylene, polyethylene, polyester, rayon, cotton, and in a mixed form or in the form of monocomponent, bicomponent fiber. For example, Pegas a.s (Czech Republic) supplies a suitable nonwoven material based on bicomponent fibers made of Polypropylene (PP) as core and Polyethylene (PE) as sheath, with a polymer ratio: PP core 70%/PE sheath 30%. A pigment is introduced within the PP core of the fiber during the manufacture of the non-woven.

As represented in FIG. 2, the lateral zones may be formed by two strips of materials 16, 18 (sometimes referred to as "lateral topsheet strips") attached to the surface of the topsheet layer 12, to form a so called hybrid topsheet as described, for example, in WO 93/09744 (Procter & Gamble) and U.S. Pat. No. 5,333,991 (Kimberly-Clark). These lateral topsheet strips may be attached by any conventional means to the underlying layer, for example embossing (e.g. thermal bonding), gluing or a combination both.

The lateral zones may take the form of two generally parallel strips extending substantially along the whole length of the longitudinal sides 101, 102 of the article. As represented in FIG. 3, the outwardly facing edge 162, 182 of the lateral zones may be contiguous to the longitudinal sides 101, 102 of the article on its periphery. The inwardly-facing edge of the lateral strips 163, 183 may be linear or non linear. In particular the inwardly facing edges may form a pattern comprising repeating waves. In one embodiment, this wavy pattern has the shape of a wave propagating in the longitudinal direction of the article. All kind types of waves may be used, such as sine waves, sawtooth waves, square waves, etc. . . . although waves which are smooth i.e. without sharp angles, such as sine type waves are preferred. The lateral topsheet strips 16, 18 may or may not be mirror image of each other relative to the longitudinal centerline L or transversal centerline T.

In the embodiment represented on FIG. 1, the central fluid acquisition zone encompasses the longitudinal centerline (L) so that the first lateral zone is on one side of the longitudinal centerline (L) and the second lateral zone is on the other side. In another embodiment shown on FIG. 5, the central fluid acquisition zone encompasses the transversal centerline (T) so that the first lateral zone is on one side of the transversal centerline (T) and the second lateral zone is on the other side. The second embodiment may be advantageous when the production line is in the so called "beta" configuration, i.e. when the article is orientated perpendicular in its length to the machine direction.

Constructions other than attaching strips of nonwoven material to the topsheet are possible to provide the article with lateral zones according to the invention. For example an underlying layer such as the backsheet may be folded around the absorbent structure to provide these, as exemplified in GB 2,214,907 (Smith & Nephew) or EP 523,683 A1 (Kimberly-Clark). It is also possible but not preferred to attach or fold the material of the lateral zones under the topsheet, for example between the topsheet and secondary topsheet or the absorbent structure when present.

In all the aspects of the invention, it may be advantageous that the lateral zones have a certain amount of opacity to mask underlying stains present underneath, for example of the surface of the absorbent structure, or for providing the desired appearance. This opacity may be provided at least in part by introducing pigments in the nonwoven material. The opacity of a material may be determined as described below.

In a first aspect of the invention, the lateral zones are visually discernible from the central acquisition zone. The inventors have found that it was possible to achieve this result in a practical and economical way by using a nonwoven material comprising a colored pigment to form the lateral zones. By visually discernible we mean that a person without vision disability such as color blindness and having a good vision in both eyes (10/10) holding the article at a distance of about 50 cm in a closed room lit with a 100 W incandescent light bulb on a ceiling of average height can recognize the presence of lateral zones which contrast with the central acquisition zone. In one embodiment, the lateral zones may be made such that at least one of the absolute values of the a* and/or b* parameters as measured on the lateral zones is above 0.5 or even above 1.

The colored pigment provides at least partially for the visual contrast with the central acquisition zone which may be substantially white. As is known in the art, pigments are colored, black, white or fluorescent particulate organic and inorganic solids which are usually insoluble in, and essentially physically and chemically unaffected by the vehicle or substrate in which they are incorporated. They alter appearance by selective absorption and/or by scattering of light. The term "colored pigment" encompasses any pigments suitable for imparting a non-white color to nonwoven material. This term therefore does not include "white" pigments such as $TiO_2$ which are typically added to the layers of conventional sanitary articles to impart them with a white appearance. Example of colored pigment is carbon black however it may be preferred to use non-black pigments which provide a more subtle tint in the pastel range.

Pigments are usually dispersed in vehicles or substrates for application, as for instance in inks, paints, plastics or other polymeric materials. Pigments retain a crystal or particulate structure throughout the coloration process. As result of the physical and chemical characteristics of pigments, pigments and dyes differ in their application; when a dye is applied, it penetrates the substrate in a soluble form after which it may or may not become insoluble. When pigments are used to color or opacify a substrate, the finely divided insoluble solids remain throughout the coloration process.

Compounding is the typical process by which color or additives are added to a basic thermoplastics material. This usually involves melting the thermoplastics material then mixing it with the required pigments and/or additive material in an extruder. The polymer melt is then extruded and chopped into pellets as it cools, which can then be used directly by the plastics processor. An associated process is masterbatch. This is where a high concentration of pigment and/or additives are dispersed in a carrier medium which can then be used directly by the processor in small quantities to pigment or modify the virgin polymer material. The pigment is added at high concentration into the carrier (e.g. polypropylene resin) supplied in pellets. The colored masterbatch is mixed to the matrix made of virgin resin in the nonwoven line at an add-on level needed to reach the desired color on the final material. The pigments may for example be introduced in a polypropylene master batch to obtain a pigmented bicomponent nonwoven. An example of suitable "masterbatch" material that can be introduced is Pantone color 270 Sanylen violet PP 42000634 ex Clariant, which is a PP resin with a high concentration of violet pigment. Typically, the amount of pigments introduced by weight of non-woven material after the compounding may be of from 0.3%-2.5%.

The color of the lateral zones can be characterized by their $L^*$, $a^*$ and $b^*$ values as measured with the CIELAB color scale. It may be preferred that the hue of the color of the lateral zones may be selected in the blue or green region rather than in the yellow or red region for aesthetic purpose. Furthermore it has been found that blue and green pigmented nonwoven may better be able to hide underlying stains of blood or urines. Thus the measured $a^*$ and $b^*$ values may be advantageously such that the relation $b^* \leq -a^*$ is fulfilled. This relation may also be expressed in term of angles values reported to the horizontal color disc represented on FIG. 7. Taking any color on the $+a^*$ axis as having a ω ("omega") angle of 0, any color on the $+b^*$ as having a ω angle of +90° and so forth, and in that case the relation $b^* \leq -a^*$ is equivalent to having a ω angle of from 135° to 315°. It was found that colors in the blue or lilac tone were even more preferable, for which an angle ω of from 220° to 310° is suitable, more precisely of from 257° to 302°.

The presence of lateral zones made of a pigmented nonwoven material according to the first aspect of the invention may be beneficial in a number of ways. The inventors have found that the lateral zones according to the first aspect of the invention provide a visually satisfactorily and distinctive appearance in a cost effective manner compared to other method such a directly printing a composition on one of the layer of the article. Color printing of lateral zones was found more difficult and costly than using pigmented nonwoven lateral zones because possible problems in keeping a color printing machine aligned with the production line and possible contamination of the production line by the ink. Furthermore the pigmented lateral zones are beneficial because they can mask the underlying periphery of the absorbent structure and convey an impression of reinforced side leakage protection to the user. Another advantage of using nonwoven pigmented materials is that there is very little, if any, color transfer from the article to the skin of the user, even when the colored material is directly at the surface of the product and may enter in direct contact with the skin of the user. It was found advantageous to use nonwoven materials made of bicomponent fibers wherein the colored pigment is present in the core of the fibers.

The first aspect of the invention also provides an article with improved appearance of the product after use. It was found that underlying stains on the surface of the absorbent structure could be at least partially hidden by the color pigmented non-woven material, thus improving the appearance of a soiled product. As discussed earlier, gradient cores are capable of distributing the fluid first vertically towards the bottom of the core where it then spreads in the horizontal plane. Gradient core have a tendency to spread lower intensity stains over a larger surface around the point of impact than conventional absorbent structure, and the first aspect of the invention provides particular benefits when a gradient core is used as absorbent structure in potentially masking part of this aureole. This also the case when non-gradient cores are used but to a lesser extent.

In order to further improve the benefits provided as discussed above, it may be preferred that the lateral zones 161, 181 are at least partially above the absorbent structure 15. As represented in the Figures, the pigmented nonwoven materials may extend from the periphery of the article, in particular its lateral edges 101, 102 to a position situated above the core 15, i.e. overlapping at least a portion of the core.

It may be preferred that the lateral topsheet strips are made of a material having water-repelling properties, in other words an hydrophobic material, to help preventing side leakage or the re-wet of the body facing surface of the article. This property is more particularly described in the second aspect of the invention, which will now be discussed in further details below.

In a second aspect of the invention, which may be combined with the first aspect or used independently, the lateral zones are made of an hydrophobic nonwoven material, the absorbent structure comprises a gradient core and the lateral zones are at least partially situated above the absorbent structure.

The hydrophobic non-woven material may preferably be inherently hydrophobic without further treatment as will be the case for most plastic materials, for example polyethylene, polypropylene and their mixtures and combinations (as in a "bico", i.e. a bicomponent fiber). A suitable hydrophobic material may be of the type comprising bicomponent fibers made of Polypropylene (PP) as core and Polyethylene (PE) as sheath. Such a polymer is for example available from, Pegas a.s (Czech Republic) with a polymer ratio: PP core 70%/PE sheath 30%. This material has a fiber denier (weight of single strand of fiber 9000 meters long) of 2.0 denier and fiber diameter of about 18÷20 micron. No additive and/or treatment are required as the polymers (PP, PE . . . ) are hydrophobic in nature. Other non-woven materials which are not inherently hydrophobic may be treated for example by the application of a composition comprising a hydrophobic component.

The hydrophobic lateral zones used in the second aspect of the invention were found to be particularly useful when a gradient core is present. It was found that gradient cores have the tendency to spread the absorbed liquid to a wider area than conventional absorbent core. As a result, there is a higher probability that the stains will reach the edge of the core than with traditional cores. The lateral zones claimed in the second aspect of the invention, which are at least partially situated above the lateral edges of the core, may provide a barrier from bodily fluid rewet on the lateral edges of the articles. This is because the hydrophobic character of the nonwoven material is capable of keeping the fluid from traversing them to rewet the surface of the article. It may be preferred to have embossed lateral hydrophobic zones, because the apertures created by these embossments will be able to provide a route through the hydrophobic nonwovens to the absorbent structure. It was found that such embossments did not seriously impact the anti-rewet properties of the lateral zones.

In the second aspect of the invention, the hydrophobic nonwoven may also be pigmented as discussed above. This has the additional benefit of further providing stain masking properties to the lateral zones. Because the stains on the surface of gradient core are of lower intensity but larger, it was found that this masking properties was particularly useful to effectively hide at least partially the underlying stains which extend to the lateral zones of the article.

Absorbent Structure—Gradient Core

The articles of the invention comprise an absorbent structure (also called "core") 15 disposed between the topsheet 12 and the backsheet 14. As used herein, the term "absorbent structure" refers to a material or combination of materials suitable for absorbing, distributing, and storing aqueous fluids such as urine, blood, menses, and other body exudates.

The size and shape of the absorbent structure can be altered to meet absorbent capacity requirements, and to provide comfort to the wearer. As with other elements of the articles of the invention, there are no particular requirements for the absorbent core and any standard liquid-absorbent material known in the art for use in absorbent articles will normally be suitable. However it may be preferred to use a gradient core as absorbent structure, as discussed above.

Non-limiting examples of liquid-absorbent materials suitable for use as the absorbent structure include comminuted wood pulp which is generally referred to as airfelt; creped cellulose wadding; absorbent gelling materials including superabsorbent polymers such as hydrogel-forming polymeric gelling agents; chemically stiffened, modified, or cross-linked cellulose fibers; meltblown polymers including co-form; synthetic fibers including crimped polyester fibers; tissue including tissue wraps and tissue laminates; capillary channel fibers; absorbent foams; absorbent sponges; synthetic staple fibers; peat moss; or any equivalent material; or combinations thereof. The absorbent structure, as the article itself, may be generally planar, i.e. does not have a significant variation in thickness.

Typically the absorbent structure is rectangularly shaped, for ease of manufacturing. However, it may be differently shaped, for example there is frequently a wearer preference for an absorbent structure which is narrower at the center than at the ends, to comfortably accommodate the legs, and obviate or minimize occurrences of bunching or wadding of the core. Oval shaped core have been proposed (e.g. WO 2005/084596). Further generic and specific information regarding absorbent structures can be found for example in WO 0207662A1 and WO 09119471.

The term "gradient core" as used herein designates the type of absorbent structure, usually obtained by an airlaid process, which are provided with anisotropic properties in the vertical direction for fast acquisition of the fluid in the vertical direction, i.e. towards the bottom of the core. This is generally achieved by providing a unitary article having a gradient of density or capillarity (normally both) in the vertical direction.

The word "unitary" as used herein refers to a single structure, which despite potential internal variations of physical and/or chemical characteristics is provided such that it cannot be separated into individual layers. Absorbent structures made from a number of layers, which are joined to each other by macroscopic mechanical or adhesive means, are well know and not uncommon in the practical embodiments of absorbent articles available to consumers. Such structures, however, are also not considered unitary in the sense of the present invention since they are formed from individual layers that, albeit sometimes with difficulty, can be separated from each other again.

Examples of gradient cores can be found in the following exemplary patent documents: WO 03/090656A1, U.S. 2002/007169, WO 00/74620. As mentioned in WO 03/090656A1, gradient cores normally show a density gradient from the wearer facing surface towards the garment facing surface of the absorbent structure. This gradient coincides with a gradient of capillarity with the largest capillaries in the upper layer, followed by capillaries of reducing sizes towards the lower layer throughout the thickness of the gradient core. Both, the capillary as well as the density gradient are particularly beneficial for the absorbent performance as liquid is driven into the material and not easily released from it, but stored in the storage core. This also has the surprising effect of providing an unsurpassed masking effect for the absorbent structure in that liquids, such as menstrual fluid or urine of older people having a rather strong yellowish color, will penetrate deep into the structure but before being distributed within the horizontal plane of the structure, thereby displaying on the outer surface a reduced visibly detectable stain size for the same kind of deposition when compared with conventional structures or even the same combination of layers but adhesively attached to each other.

A preferred type of gradient cores may be made according to the teaching of WO 03/090656A1. This type of gradient cores is of unitary construction and has a wearer facing and a garment facing surface. The garment facing surface is immediately adjacent the backsheet and the wearer facing surface is immediately adjacent the topsheet. These gradient cores have a fibrous, stratified, layered structure of at least 3 layers in which all layers are unified into the unitary core by a single thermal combining step or a single felting step or both steps combined, but preferably without the use of adhesive between layers.

A preferred suitable of core may comprise a first outermost layer forming the wearer facing surface, which is provided from a mixture of bi-component fibers and cellulose or viscose fibers, preferably non-softened cellulose fibers, and the first layer has a weight fraction of the overall core construction of 10%-30%, a second outermost layer forming the garment facing surface of the core, the second layer being provided by softener treated cellulose fibers having a weight fraction of the overall core of 30%-50%, and a surface binder, preferably a latex, on the garment facing surface of the core in an amount of 0%-2% by weight of the core, and at least one inner layer, sandwiched between the first and the second layer, the inner layer comprising non-softened cellulose fibers, optionally bi-component fibers, and further comprising super absorbent material, the inner layer having a weight fraction of the overall core of 30%-50%.

This type of gradient core may be preferably free of binder material, except for the bi-component fibers in the core layers and the surface binder on the garment facing surface of the core.

Backsheet

The backsheet 14 may be any flexible, liquid resistant, and liquid impervious material. The backsheet prevents discharges collected by and contained in the sanitary napkin, and particularly discharges absorbed by the core, from escaping the sanitary napkin and soiling the clothing and bedding of the wearer. Preferably the backsheet is not noisy, to provide discretion for the wearer. In some executions, a secondary backsheet (discussed below) may be placed intermediate the core and the backsheet to second the backsheet, for example to provide liquid imperviousness.

Any conventional backsheet materials may be used within the invention, such as polyolefinic films. The backsheet may be impervious to malodorous gases generated by absorbed bodily discharges, so that the malodors do not escape. The backsheet may or may not be breathable. A low density polyethylene backsheet about 0.01 to about 0.08 millimeters in thickness, preferably about 0.05 millimeters in thickness, is usual. A polyethylene film, such as is sold by the Tredegar Corporation of Terre Haute, Ind., under model X-813 may be used. Further, the backsheet may be made of a soft cloth like material which is hydrophobic relative to the topsheet, e.g. a polyester or polyolefinic fiber backsheet.

The topsheet and the backsheet are preferentially peripherally joined using known techniques, either entirely so that the entire perimeter of the sanitary article is circumscribed by such joinder or are partially peripherally joined at the perimeter. The term "joined" refers to the condition where a first component is affixed, or connected, to a second component either directly; or indirectly, where the first component is affixed, or connected, to an intermediate component which in turn is affixed, or connected, to the second component. The joined condition between the first component, and the second component, is intended to remain for the life of the sanitary napkin. Conversely, components are considered "removably affixed" if the components may be detached and separated from each other without destruction or unintended gross deformation of either.

Any joined arrangement that provides for capture of the absorbent structure intermediate the topsheet and the backsheet and a unitary assembly is suitable. Such an assembly has two mutually opposed major faces, one defined by the topsheet and one defined by the backsheet.

The outwardly oriented (garment facing) face of the backsheet may further comprise means for attaching the sanitary napkin to the undergarment of the wearer. Pressure sensitive adhesive has been commonly found to work well for this purpose. Preferably a strip of longitudinally oriented adhesive provides good protection against either the front or the back of the sanitary napkin becoming detached from the wearer's undergarment. The adhesive strip may be continuous or intermittent. A particularly preferred arrangement utilizes two longitudinally oriented strips, one on each side of the longitudinal centerline.

The backsheet typically extends across the whole of the absorbent structure and can extend into and form part of or all of the sideflaps, side wrapping elements or wings, when present.

Secondary Topsheet

The articles of the invention may optionally comprise a secondary topsheet layer 20 intermediate the topsheet 12 and the absorbent core 15.

Such a secondary layer may be manufactured from a wide range of materials such as woven, nonwoven materials, polymeric materials such as apertured formed thermoplastic films, apertured plastic film, hydro formed thermoplastic films, porous foams, reticulated foams, reticulated thermoplastic films and thermoplastic scrims. Any material described herein before for the topsheet can be used for the secondary layer. In a preferred embodiment, this secondary topsheet layer underlies the apertured topsheet on the entire surface thereof, i.e., the secondary layer extends to the periphery of the topsheet so that the secondary layer underlies the topsheet on the entire inner surface of the topsheet.

The purpose of the secondary topsheet is normally to readily transfer the acquired body fluid from the topsheet to the absorbent core, the transfer of fluid occurring not only vertically in the thickness of the secondary topsheet, but also along the length and the width directions of the absorbent product. This helps the fluid capacity of the underlying storage layer to be fully utilized. Although preferred, the presence of secondary topsheet is however optional Secondary Backsheet The articles of the invention may comprise a secondary backsheet layer 22 intermediate the absorbent core 15 and the backsheet layer 14. The use of a secondary backsheet is particularly indicated in presence of an air permeable backsheet. The purpose of the secondary backsheet is to retard or prevent liquid from passing from the absorbent core to the outside of the product, while allowing free air flow through it. A preferred example of secondary backsheet is a resilient three dimensional polymeric web, which consist of a liquid impervious film which has apertures forming capillarity or cones. The film with capillaries or cones is oriented such that the apexes of the cones face the absorbent core, this to prevent passage of fluid. The capillaries or cones can have a slanted shape in order to partly close or completely close when compressed.

Release Paper

The adhesive coated on the backsheet surface are typically provided with a protective cover, which is removed prior to use. The protective cover may be a silicone coated release paper, a plastic film or any other easily removable cover. The protective cover may be in a single piece or in a multitude of pieces, e.g. to cover the individual adhesive areas. It also can perform other functions such as providing individualized packaging for the article or provide a disposal function. Any commercially available release paper or film may be used. Suitable examples include BL 30 MG-A SILOX EI/O, BL 30 MG-A SILOX 4 P/O available from Akrosil Corporation, and M&W films available from Gronau in Germany, under the code X-5432.

Method of Manufacture

The absorbent articles of the present invention may comprise the usual layers or components normally found in commercially available standard articles which may be joined together by standard means such as embossing (e.g. thermal bonding) or gluing or combination of both, and the articles may be produced industrially by conventional means.

CIE L*a*b* Color Scale

The CIE L*a*b* (or CIELAB) Color Scale is an internationally recognized three-dimensional based system for describing colors. This system was adopted by the International Commission on Illumination—abbreviated as CIE from its French title Commission Internationale de l'Eclairage. CIE Publication 15.2 (1986), Section 4.2, contains details on this color scale.

Figure 7:
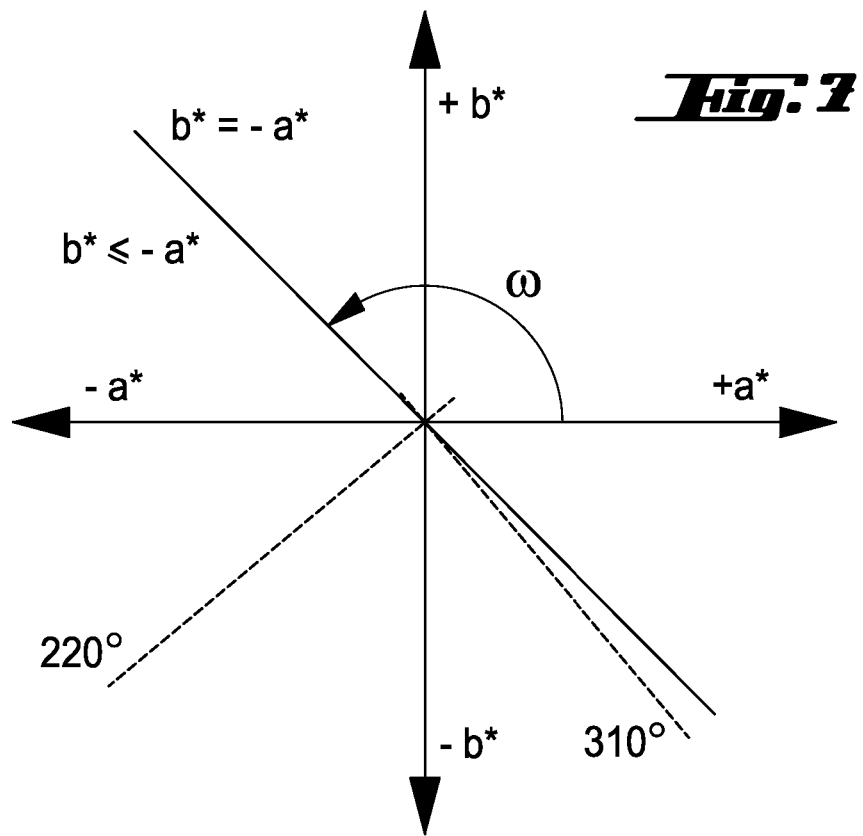
FIG. 7 shows the horizontal plane of the color sphere for L=50.

The CIELAB color space is organized in a spherical form with the L* axis running from top to bottom and the a* and b* axis being placed in an horizontal plane, see FIG. 7. In general, CIE L* scale values are units of light reflectance measurement, and the higher the value is, the lighter the color is since a lighter colored material reflects more light. The L* scale contains 100 equal units of division, absolute black is at the bottom of the scale (L=0) and absolute white is at the top of the scale (L=100). Thus in measuring L* values of the materials used in the absorbent articles according to the present invention, the lower the L* scale value, the darker the material. The a* axis is the axis red/green (+a*=red, −a*=green), while b represents the axis yellow/blue (+b*=yellow, −b*=blue).

The L*, a* and b* values can be measured using any suitable equipment, for example the colorimeter MINOLTA mode CR-300 instrument (available from the Minolta Company, Japan) which provides the coordinates L*, a*, b* and from which the ΔE* value between two color points can be determined.

It is to be understood that the L*a*b* value claimed or described herein in relation with the materials of interest (e.g., lateral zones or central zone) are measured on the material taken in-situ within the finished absorbent article and are not measured on the material independently of its background unless otherwise stated, as is also possible. Because most of the materials considered have some transparency, their L*, a*, and b* value are influenced to an extent by the underlying layer(s).

Opacity Index

The nonwoven materials forming the lateral zones advantageously have a minimum opacity so as to be able to mask underlying stains. The opacity of the materials considered can be influenced by a number of factors, the main one being the nature of the fibers, the presence of light absorbing materials such as pigments or dyes, and the thickness of the nonwoven material. Pigments were found to be capable to improve the opacity of the nonwovens material in which they were incorporated.

The opacity of a given sample of nonwoven material may be characterized by passing a beam of emitted light through the sample and measuring the resulting transmitted light, for example using a standard spectrophotometer apparatus. The Opacity Index (O.I.) may then be defined as:

$$O.I.\ (\%) = 100 - \frac{\text{intensity of the transmitted light}}{\text{intensity of emitted light}} \cdot 100$$

For most materials, the nature of the light used will influence the amount of light transmitted, as the transmittance of a given material or substance depends on the wavelength of the light emitted. Colorimeters are therefore normally provided with a light emitter which can be set up at different wavelength values.

The Opacity Index used herein is measured with the apparatus set at a wavelength of 745 nm, which appears red and was found to replicate approximately the appearance of menses. A suitable apparatus is for example a Perkin-Elmer lambda 20 UV-Visible spectrophotometer.

The Opacity Index of the nonwoven materials to be used in the present invention may be of at least one of the following values: 50%, 60%, 70%, 80% or more as measured with light at a wavelength of 745 nm.

The presence of pigments, especially colored pigments, was found to increase the opacity of the nonwoven materials. For example, The O.I. of a nonwoven sheet of material made of Pegas bicomponent fibers discussed above was tested with the violet Pantone pigments (1.1% by weight of PP). The average results (5 iterations) for the pigmented material was 83.6%.

Hydrophobicity Value

The determination of the Hydrophobicity of a substrate can be determined by measuring the Contact Angle formed by a drop of de-ionized water in contact with the surface of the substrate. A suggested method employs a Drop Shape Analysis instrument such as a Kruss DSA 100, which automatically gently lays drops of water 30 though a syringe 32 on planar and perpendicular substrate samples. The drops have a standardized volume of 6±1 μl. The measurements are normally made at room temperature (23° C.). This instrument is fitted as standard with a camera and computer with picture-analysis software. The contact angle α is automatically measured according to the Young-Laplace Method. Results are normally expressed as the average of at least 6 drop contact angle measurements. FIG. 8 shows a drop of water deposited on the surface of a hydrophobic material suitable to be used as lateral topsheet strips 16, 18 according to this measurement method.

As used herein, the term "hydrophobic" qualifies a nonwoven substrate for which the measured contact angle on this area according to this method is of at least 90°. "Hydrophilic" relates to a contact angle below 90°.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

What is claimed is:

1. An absorbent article for collecting bodily fluid, the absorbent article comprising a topsheet, a backsheet and an absorbent structure situated between the topsheet and the backsheet,
   wherein the topsheet comprises:
   i) a layer of topsheet material extending from one longitudinal side of the absorbent article an opposing longitudinal side of the absorbent article, the layer of topsheet material comprising a central fluid acquisition zone,
   ii) a first visually discernible lateral zone situated on one side of the central fluid acquisition zone and overlaying a first portion of the layer of topsheet material in a substantially parallel manner, and
   iii) a second visually discernible lateral zone situated on an opposite side of the central fluid acquisition zone and overlaying a second portion of the layer of topsheet material in a substantially parallel manner,
   wherein each of the first and second lateral zones is formed by a nonwoven material comprising a colored pigment, wherein the nonwoven material comprises bicomponent fibers comprising a core of polypropylene and a sheath of polyethylene, and wherein the colored pigment is present in the polypropylene core;
   wherein the layer of topsheet material is different than the nonwoven material of the first and second lateral zones.

2. An absorbent article according to claim 1 wherein the layer of topsheet material comprises a nonwoven material.

3. An absorbent article according to claim 1 wherein the first and second lateral zones are at least partially situated above the absorbent structure.

4. An absorbent article according to claim 1 wherein the topsheet is conceptually divided in its length in two halves by a longitudinal centerline and wherein the central fluid acquisition zone substantially encompasses the longitudinal centerline so that the first lateral zone is on one side of the longitudinal centerline and the second lateral zone is on the other side.

5. An absorbent article according to claim 1 wherein the nonwoven material forming the lateral zones has an Opacity Index of a least 50%, measured at 745 nm.

6. An absorbent article according to claim 1 wherein the nonwoven material is hydrophobic.

7. An absorbent article according to claim 1 wherein the first and second visually discernible lateral zones extend to the periphery of the absorbent article.

8. An absorbent article according to claim 1 wherein the absorbent structure comprises a gradient core.

9. An absorbent article according to claim 1, wherein the first and second lateral zones comprise a color having a* and b* values wherein b*≤−a*.

10. An absorbent article according to claim 1, wherein an inwardly-facing longitudinal edge of the first and second lateral zones is linear.

11. An absorbent article according to claim 1, wherein an inwardly-facing longitudinal edge of the first and second lateral zones is non linear.

12. An absorbent article according to claim 1, wherein the first and second lateral zones comprise a lilac tone.

13. An absorbent article according to claim 1, wherein the first and second lateral zones comprise discrete strips of material.

14. An absorbent article according to claim 13 wherein the strips of material comprise a nonwoven.

15. An absorbent article according to claim 1, wherein the central fluid acquisition zone is substantially white.

16. An absorbent article according to claim 1, wherein the central fluid acquisition zone comprises an L* Hunter value of greater than or equal to 90.

17. An absorbent article according to claim 1, wherein the central fluid acquisition zone defines between 30% and 70% of a body-facing surface of the absorbent article.

18. An absorbent article according to claim 1, wherein the topsheet further comprises longitudinally-extending embossments proximate the first and second lateral zones.

19. An absorbent article according to claim 1, wherein the first and second lateral zones comprise a color having a* and/or b* values that are above 0.5.

20. An absorbent article according to claim 19 wherein an inwardly-facing longitudinal edge of the first and second lateral zones is linear.

21. An absorbent article according to claim 19 wherein an inwardly-facing longitudinal edge of the first and second lateral zones is non linear.

22. An absorbent article according to claim 19 wherein the first and second lateral zones comprise a lilac tone.

23. An absorbent article according to claim 19 wherein the first and second lateral zones comprise discrete strips of material.

24. An absorbent article according to claim 23 wherein the strips of material comprise a nonwoven.

25. An absorbent article according to claim 19 wherein the central fluid acquisition zone defines between 30% and 70% of a body-facing surface of the absorbent article.

26. An absorbent article according to claim 19 wherein the topsheet further comprises longitudinally-extending embossments proximate the first and second lateral zones.

27. An absorbent article according to claim 1, wherein the first and second lateral zones comprise a color having an omega angle of 135° to 315°.

28. An absorbent article according to claim 27 wherein an inwardly-facing longitudinal edge of the first and second lateral zones is linear.

29. An absorbent article according to claim 27 wherein an inwardly-facing longitudinal edge of the first and second lateral zones is non linear.

30. An absorbent article according to claim 27 wherein the first and second lateral zones comprise a lilac tone.

31. An absorbent article according to claim 27 wherein the first and second lateral zones comprise discrete strips of material.

32. An absorbent article according to claim 31 wherein the strips of material comprise a nonwoven.

33. An absorbent article according to claim 27 wherein the central fluid acquisition zone is substantially white.

34. An absorbent article according to claim 27 wherein the central fluid acquisition zone comprises an L* Hunter value of greater than or equal to 90.

35. An absorbent article according to claim 27 wherein the central fluid acquisition zone defines between 30% and 70% of a body-facing surface of the absorbent article.

36. An absorbent article according to claim 27 wherein the topsheet further comprises longitudinally-extending embossments proximate the first and second lateral zones.

37. An absorbent article according to claim 1, wherein the first and second lateral zones have an omega angle of 220° to 310°.

38. An absorbent article according to claim 1, wherein the first and second lateral zones have an omega angle of 257° to 302°.

39. An absorbent article according to claim 1, wherein the first and second lateral zones are colored to have a color selected in the blue or green region of the CIELAB color scale and not the yellow or red region of the CIELAB color scale, and wherein the central fluid acquisition zone is substantially white.

40. An absorbent article according to claim 39 wherein the first and second lateral zones comprise a lilac tone.

* * * * *